US011097078B2

(12) United States Patent
Kochman

(10) Patent No.: US 11,097,078 B2
(45) Date of Patent: Aug. 24, 2021

(54) METHOD AND SYSTEM FOR FACILITATING THE TRANSITION BETWEEN A CONSCIOUS AND UNCONSCIOUS STATE

(71) Applicant: Cary Kochman, Wilmette, IL (US)

(72) Inventor: Cary Kochman, Wilmette, IL (US)

( * ) Notice: Subject to any disclaimer, the term of this patent is extended or adjusted under 35 U.S.C. 154(b) by 299 days.

(21) Appl. No.: 16/272,443

(22) Filed: Feb. 11, 2019

(65) Prior Publication Data

US 2020/0094013 A1    Mar. 26, 2020

Related U.S. Application Data

(60) Provisional application No. 62/736,786, filed on Sep. 26, 2018.

(51) Int. Cl.
*A61M 21/00* (2006.01)
*A61B 5/00* (2006.01)
*A61B 5/024* (2006.01)

(52) U.S. Cl.
CPC ......... *A61M 21/00* (2013.01); *A61B 5/02438* (2013.01); *A61B 5/681* (2013.01);
(Continued)

(58) Field of Classification Search
CPC .. A61M 2021/0016; A61M 2021/0027; A61M 2205/80; A61M 2205/609; A61M 2205/502; A61M 2230/08; A61M 2021/0066; A61M 2230/50; A61M 2021/005; A61M 2230/30; A61M 2021/0083; A61M 2205/505;
(Continued)

(56) References Cited

U.S. PATENT DOCUMENTS 5,304,112 A * 4/1994 Mrklas .............. A61M 21/0094
434/236
6,702,767 B1 * 3/2004 Douglas ............ A61M 21/0094
600/21
(Continued)

FOREIGN PATENT DOCUMENTS

KR          100791371 B1     1/2008

OTHER PUBLICATIONS

Korean Intellectual Property Office, International Search Report for Application No. PCT/US2019/051945, dated Jan. 23, 2020, 3 pages.
(Continued)

*Primary Examiner* — Navin Natnithithadha
*Assistant Examiner* — Sunita Reddy
(74) *Attorney, Agent, or Firm* — Greensfelder, Hemker & Gale, P.C.; Richard C. Himelhoch

(57) ABSTRACT

A system and method for facilitating and maintaining various states of a user consciousness, including the transition between a conscious and unconscious state, is provided. The system and method include use of a smart device having a user interface, a biometric sensor coupled to a user and configured to transmit the user's biometric data to the smart device and an environmental sensor configured to transmit environmental data to the smart device. The smart device controls one or more environmental systems proximate the user and an audio/visual device proximate the user to facilitate transitioning the state of the user.

17 Claims, 2 Drawing Sheets

(52) U.S. Cl.
CPC .... *A61B 5/7475* (2013.01); *A61B 2560/0242* (2013.01); *A61M 2021/0016* (2013.01); *A61M 2021/0027* (2013.01); *A61M 2021/0044* (2013.01); *A61M 2021/0066* (2013.01); *A61M 2021/0083* (2013.01); *A61M 2205/3306* (2013.01); *A61M 2205/3368* (2013.01); *A61M 2205/3375* (2013.01); *A61M 2205/3569* (2013.01); *A61M 2205/502* (2013.01); *A61M 2230/06* (2013.01)

(58) Field of Classification Search
CPC .............. A61M 2230/42; A61M 21/00; A61M 2205/42; A61M 2230/06; A61M 2230/63; A61M 2205/3368; A61M 2205/3375; A61M 2205/3569; A61M 2205/3306; A61M 2230/10; A61M 21/02; A61M 2021/0044; A61M 2205/3561; A61M 2230/005; A61B 5/681; A61B 5/02438; A61B 5/7475; A61B 2560/0242
USPC ...................................... 600/26–28
See application file for complete search history.

(56) References Cited

U.S. PATENT DOCUMENTS

| | | |
|---|---|---|
| 7,716,572 B2 | 5/2010 | Beauregard et al. |
| 8,306,976 B2 | 11/2012 | Handman et al. |
| 8,644,550 B2 | 2/2014 | Basson et al. |
| 8,650,094 B2 | 2/2014 | Cai et al. |
| 8,704,760 B2 | 4/2014 | Kang et al. |
| 9,335,818 B2 | 5/2016 | Ye et al. |
| 9,721,551 B2 | 8/2017 | Silverstein |
| 9,729,910 B2 | 8/2017 | Lind et al. |
| 2005/0143617 A1* | 6/2005 | Auphan ............... A61B 5/4815 600/26 |
| 2006/0106275 A1* | 5/2006 | Raniere ................. A61M 21/02 600/26 |
| 2007/0083079 A1* | 4/2007 | Lee ....................... A61M 21/00 600/27 |
| 2007/0106672 A1 | 5/2007 | Sighart et al. |
| 2007/0196802 A1 | 8/2007 | Beletski et al. |
| 2010/0087701 A1* | 4/2010 | Berka ................... A61M 21/02 600/27 |
| 2010/0331606 A1* | 12/2010 | Wong .................. A61M 16/161 600/27 |
| 2011/0004047 A1* | 1/2011 | Braspenning .......... A61B 5/165 600/27 |
| 2011/0010014 A1 | 1/2011 | Oexman et al. |
| 2011/0190594 A1 | 8/2011 | Heit et al. |
| 2011/0295083 A1* | 12/2011 | Doelling ................. A61B 5/11 600/301 |
| 2013/0234823 A1* | 9/2013 | Kahn ..................... A61B 5/024 340/3.1 |
| 2014/0207292 A1* | 7/2014 | Ramagem .......... G05D 23/1902 700/278 |
| 2014/0276112 A1* | 9/2014 | Fung ........................ A61B 8/02 600/479 |
| 2014/0316192 A1* | 10/2014 | de Zambotti ........ A61B 5/0205 600/28 |
| 2015/0067708 A1 | 3/2015 | Jensen et al. |
| 2015/0173671 A1* | 6/2015 | Paalasmaa ........... A61B 5/6891 600/301 |
| 2015/0258301 A1* | 9/2015 | Trivedi ................ A61B 5/6898 600/28 |
| 2015/0319479 A1 | 11/2015 | Mishra et al. |
| 2015/0320588 A1* | 11/2015 | Connor ................. A61F 7/0085 607/107 |
| 2016/0008568 A1* | 1/2016 | Attia ...................... A61B 5/486 600/28 |
| 2016/0015315 A1* | 1/2016 | Auphan ............... A61B 5/6892 600/301 |
| 2016/0088332 A1 | 3/2016 | Lind et al. |
| 2016/0136385 A1* | 5/2016 | Scorcioni ............. A47C 21/044 600/26 |
| 2016/0151603 A1* | 6/2016 | Shouldice ................ H04R 3/00 600/28 |
| 2016/0192876 A1* | 7/2016 | Proud .................... A61B 5/1118 600/595 |
| 2016/0217672 A1 | 7/2016 | Yoon et al. |
| 2016/0334121 A1* | 11/2016 | Oobayashi ............... F24F 11/77 |
| 2017/0048563 A1 | 2/2017 | Oman |
| 2017/0206569 A1 | 7/2017 | Reiley et al. |
| 2017/0319817 A1* | 11/2017 | Morishima .......... A61B 5/6824 |
| 2018/0004480 A1 | 1/2018 | Medaghri Alaoui et al. |
| 2018/0018948 A1 | 1/2018 | Silverstein |
| 2018/0050171 A1* | 2/2018 | Tabert ................. A61B 5/7455 |
| 2018/0082550 A1* | 3/2018 | Read ........................ A61B 5/01 |
| 2018/0110960 A1 | 4/2018 | Youngblood et al. |
| 2018/0207393 A1* | 7/2018 | Baek ................... A61B 5/4812 |
| 2018/0359112 A1* | 12/2018 | Lee .................. A61M 21/0094 |

OTHER PUBLICATIONS

Korean Intellectual Property Office, Written Opinion of the International Searching Authority for Application No. PCT/US2019/051945, dated Jan. 23, 2020, 7 pages.

\* cited by examiner

METHOD AND SYSTEM FOR FACILITATING THE TRANSITION BETWEEN A CONSCIOUS AND UNCONSCIOUS STATE

CROSS-REFERENCE TO RELATED APPLICATIONS

The present invention claims the benefit of U.S. Provisional Application Ser. No. 62/736,786, filed Sep. 26, 2018, the contents of which are incorporated herein by reference.

FEDERALLY SPONSORED RESEARCH OR DEVELOPMENT

N/A

FIELD OF THE INVENTION

The present invention is directed to a method and system for facilitating and maintaining various states of consciousness; and in particular, to a method and system for facilitating and maintaining the transition between one of a conscious state and an unconscious state.

DESCRIPTION OF THE PRIOR ART

From meditation to medication, many people have difficulty falling asleep and seek a means to safely, effectively, and easily drift into unconsciousness. Similarly, once asleep, many dislike the harsh blare of an alarm clock and desire a more palatable approach to waking up. A variety of methods and systems (e.g., clock radios that provide white noise, soothing sounds or music, or harsh beeping) have been utilized in the past to provide some assistance in transitioning from one state to the other.

Hypnagogia, or hypnagogic state, is the state of consciousness leading into sleep; as compared to the hypnopompic state, which is the state of consciousness leading out of sleep. The present invention provides an improved method and system for smoothly and quickly moving a user of the method or system from one state of consciousness to the other state of consciousness.

SUMMARY OF THE INVENTION

The present invention provides a method and system for facilitating and maintaining various states of consciousness. For instance, the method and system can be used for facilitating and maintaining a user's transition from a conscious state to an unconscious state. Similarly, the present invention can also be used to facilitate a user's transition from an unconscious state to an alert and conscious state. The system and method can be used to reduce anxiety, for example, during travel or hospitalization. The system and method can also be used to aid a user's focus—which can be useful for work, study or achieving a restful state.

In accordance with one aspect of the present invention, a system for facilitating a user's transition to or from one of a hypnagogic state and a hypnopompic state. The system comprises a smart device having a user interface. A "smart device" is a device, such as a computer, lap top, tablet, or even a smart phone that can access a wired or wireless network, and is capable of running applications that receive input signals or data, and can control other systems. The smart device can be voice activated or interfaced via another device or system (including one that is itself voice activated).

The smart device is configured to receive inputs from one or more biometric devices coupled to a user of the system and one or more environmental sensors proximate the user. The smart device is configured to control an audio/visual device and one or more environmental systems proximate the user based on the inputs from the biometric device(s) and environmental sensor(s) to facilitate a user transitioning to one of a hypnagogic state and a hypnopompic state to the other state.

The system includes at least a first biometric sensor coupled to a user and configured to transmit the user's biometric data to the smart device. The system also includes at least a first environmental sensor configured to transmit environmental data to the smart device. The system also includes a first environmental system coupled to the smart device where the smart device is configured to control the first environmental system to optimize the environmental system for transitioning the state of consciousness of the user. The system also includes a first audio/visual device coupled to the smart device where the smart device is configured to control audio and video output displayed on the audio/visual device to facilitate transitioning the state of the user.

The biometric sensor can be a heart rate monitor. Such monitors are routinely found on smart watches used to monitor physical activity. Other biometric sensors can include those that monitor: respiration rate; brain activity; body temperature; blood pressure; user movement, pupil dilation, etc.

The environmental sensor can be a temperature sensor for measuring the ambient temperature of the area proximate the user. Additionally, the sensors can include: a light sensor; and a sound sensor.

The first environmental system can be a heating, ventilation and air conditioning system. Additional environmental systems can include a lighting system; an olfactory device, etc.

The system can include remote sensors to monitor the user and his position (e.g., proximity to the environmental systems). These can include motions detectors/sensors, etc.

The system can also be monitored for sound and can include noise cancellation devices.

The smart device can be configured to control one or more controllable variables, such as lighting, sound, temperature, humidity, visual, audio, olfactory. In conjunction and/or coordination with user biometric devices and environmental sensors, the system facilitates a user transitioning and/or maintaining one or more states of consciousness. For example, the system can be used to transition the user to and from the hypnagogic state and the hypnopompic state.

The smart device can also be configured to receive feedback input from the user via the user interface. This can include preference information relating to the controlled audio/visual device (e.g., choice of music or video, etc.), or preferences relating to any of the other controlled environmental systems. It may also include feedback relating to the user's condition (e.g., emotive state, etc.). In some instances, the smart device is configured to control the environmental system(s) and audio/visual device(s) to create a state that invokes or produces an autonomous sensory meridian response in the user.

In accordance with another aspect of the invention, a method for facilitating a user's transition into a hypnagogic state is provided. The method comprises the steps of providing a controller (e.g., a smart device running an appropriate application) transmitting biometric data from a user to the controller, and transmitting environmental data proximate the user to the controller. The method further comprises the step of controlling an environmental device and an audio/visual device proximate the user by the controller based on the biometric data and environmental data transmitted to the controller.

The step of transmitting biometric data from a user to the controller can include providing the user with a heartrate monitoring devise, periodically measuring the user's heartrate with the device, and electronically transmitting the user's measured heartrate to the controller.

The method can also include monitoring other aspects of the user. For example, the system can employ devices (e.g., camera's coupled to the controller) for monitoring bodily movement(s), including eye movement(s), respiration, etc.

The step of transmitting environmental data proximate the user to the controller can include providing a temperature sensor proximate the user, periodically measuring the temperature with the temperature sensor, and electronically transmitting the measured temperature to the controller.

The step of controlling an environmental device and an audio/visual device proximate the user by the controller based on the biometric data and environmental data transmitted to the controller can include providing a heating device proximate the user coupled to the controller, and transmitting a signal from the controller to the heating device adjusting a temperature output of the heating device by the controller. Additionally, the step of controlling an environmental device and an audio/visual device proximate the user by the controller based on the biometric data and environmental data transmitted to the controller can include providing an audio/visual display proximate the user, and transmitting audio data and video data to the audio/visual device by the controller. By "proximate" it is meant that the device is positioned so that it can affect the user—this may vary by the type of device employed.

It is contemplated that any audio and/or visual device could be used in this system and method. Such devices could include, for example, a personal assistant device (e.g., an Alexa or Google assistant), a television screen or a projection of visual imagery, both two dimensional or three dimensional. Additionally, it is contemplated that any device that is capable of raising or lowering body temperature can be used including a warming/cooling blanket, an infrared heater, or a body connected device such as a wrist cooler.

In the method, the controller can use machine learning techniques and/or artificial intelligence programming which analyses the biometric data transmitted to the controller and the environmental data transmitted to the controller and provides a control signal to the environmental device and to the audio/visual device to optimize a user's transition into a hypnagogic state. The system can utilize such techniques and programming to improve and optimize a repeat user's experience.

Specifically, the controller can utilize machine learning and artificial intelligence programming to continually analyze any or all biometric, user, environmental and other data transmitted to the controller and thereby control and optimize all available controllable variables to enhance the desired user state. For example, the video or photos or music that are most favored by the user can be put into the environment to produce desired results. This includes personal data (e.g., playlists, personal photos/video, etc.) or public data. The system can search for and utilize such data to enable the desired user response. The flow of such stimuli can be continuous, static or montages.

The system can be set for use at a specific time(s) (e.g., to put someone to sleep and/or wake them up instead of an alarm clock). The system can assist with relaxation or meditation. It can also produce an audio or visual experience that produces particular biometric and/or emotive responses. The system can also impact mood or assist in achieving a desired emotive or meditative state, or stimulate an autonomous sensory meridian response (ASMR).

Other features and advantages of the invention will be apparent from the following specification taken in conjunction with the following Figures.

BRIEF DESCRIPTION OF THE DRAWINGS

To understand the present invention, it will now be described by way of example, with reference to the accompanying drawings in which.

DETAILED DESCRIPTION

Figure 1:
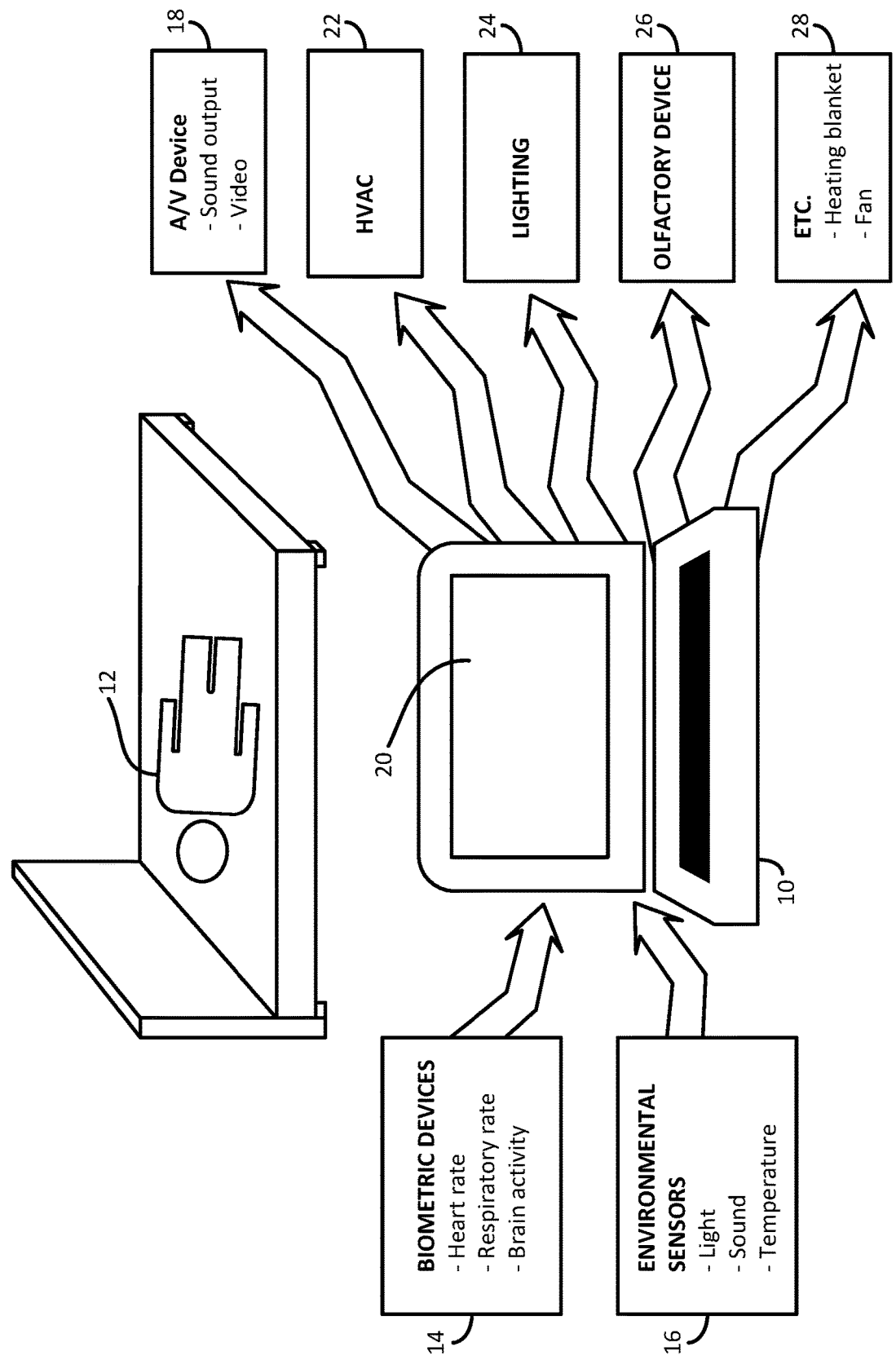
FIG. 1 is a flow chart illustrating various inputs and outputs of the method and system of the present invention.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The present system and method are provided to enable a user to achieve sleep more rapidly and/or more deeply (than typical for the individual when not using the system) from an awake (conscious) state, and may enhance any dream state. The system and method can also be used to wake an unconscious user in a more efficient and effective manner. The system can also be used to maintain or enhance various conscious states.

Referring to FIG. 1, a controller 10 is utilized to initiate and control the system and method. The controller 10 can be a smart device, such as a computer, a smart phone or tablet, or other similar devices, having an application (e.g., program) running thereon or accessible to the controller 10 (e.g., over a network connection, either wired or wireless). This can include an Alexa or Google device, or other voice activated devices.

As set forth in more detail below, the controller 10 is configured to receive various inputs relating to a user 12 of the system or method, as well as inputs regarding environmental elements proximate the user 12. The controller 10 is also configured to control various devices or provide output signals or instructions to various other systems to effectuate desired conditions for facilitating the transition of the user's state of consciousness. The controller 10 utilizes various control methods, such as algorithms that rely on feedback of the user's condition and/or environment to optimally control the output devices. The controller 10 can also use or include AI (artificial intelligence), or AI-like algorithms in this process. For particular users, the controller can be configured to learn or remember optimum output settings and/or sequences for more rapidly transitioning the user from a first state to a second state of consciousness.

In operation, the controller 10 receives biometric data about the user 12 of the system. The data can include one or more of the user's heart rate; respiration rate; brain activity; body temperature; blood pressure; etc. The data can be generated from biometric devices or sensors 14 connected to or otherwise associated with, the user 12. One such device 14 can be a smart watch. Such watches now include heart rate monitors and are routinely used for monitoring physical activity. Alternatively, other similar equipment for providing biometric feedback can be used.

The controller 10 may utilize personal medical or DNA data or other data in conjunction with any sensed biometric data to facilitate optimizing the experience.

The controller 10 can also receive data regarding the environment proximate the user through sensors 16. This can include data regarding the amount of light or noise proximate the user. It can also include other environmental data such as the room temperature, air movement (e.g., via a fan); humidity, etc.

The controller 10 can also receive inputted data from the user. This can include preferences regarding any of the controlled output systems coupled to the controller, or feedback that pertains to the user's present emotional state, etc. The user 12 could input this data directly to the controller 10 (e.g., drop down menus, or selecting various buttons/links in the application run on the controller).

The inputted or received data can be utilized by the controller to determine the state of consciousness of the user and from such determination, utilize one or more systems to facilitate transition of the state. The data can be monitored periodically or continuously in real time to determine if the state is changing or has changed. The data can be analyzed for physical and/or behavioral metrics to facilitate smoother, quicker transitions for future uses of the system by the user 12.

The controller 10 can be coupled to a variety of other systems that can affect the user (both physically and emotionally). For example, the controller 10 can control an audio and/or visual (hereafter, collectively "audio/visual" or "A/V") device 18 (the audio/visual device can be separate devices or part of the same device moreover, the audio/visual device can be included in the controller 10). The controller 10 can stream or output audio and/or visual content to the user (either using a display 20 on the controller, or a separate device) to effect the user's emotive state. The content can be selected to achieve or facilitate the transitioning of the user from one state of consciousness to another. It can also be used as an anti-anxiety device (e.g., for travel or other instances that cause anxiety in the user).

In addition to the audio/visual device 18, the controller 10 can be coupled to one or more of the heating, ventilation and air conditioning systems 22 (hereafter "HVAC") proximate the user 12. Similarly, the controller 10 can be coupled to a lighting system 24 proximate the user 12. This allows the controller 10 to control a variety of environmental factors near the user 12.

The controller 10 can be coupled to an olfactory device 26, or other devices 28 that can have some effect on the user's conscious state. These can include heating devices (e.g., blankets, wrist and neck thermal technologies), or cooling devices (cooling pillows/beds, fans), etc. In one instance where the controller 10 is used to wake a user from an unconscious state, the controller 10 can be coupled to a coffeemaker proximate the user 12.

The present system and method for facilitating a user's transition from a first state of consciousness to a second state of consciousness is part of a larger, broader invention relating to a system and method for creating an emotive sensory experience for a user. The system and method utilizes sensory and other inputs relating to the user and can be personalized to provide a bespoke experience for each user.

In accordance with another aspect of the invention, the system can be utilized in a medical setting. In such instance, the system may cooperate with and/or control an intravenous delivery system (for administering various medicines), or other medical equipment.

In one example, the system can be used with a runner or cyclist (or other aerobic activities). The system can monitor heartbeat and/or speed of the user, etc. and can select imagery and/or music to assist the user to facilitate optimum exertion.

Figure 2:
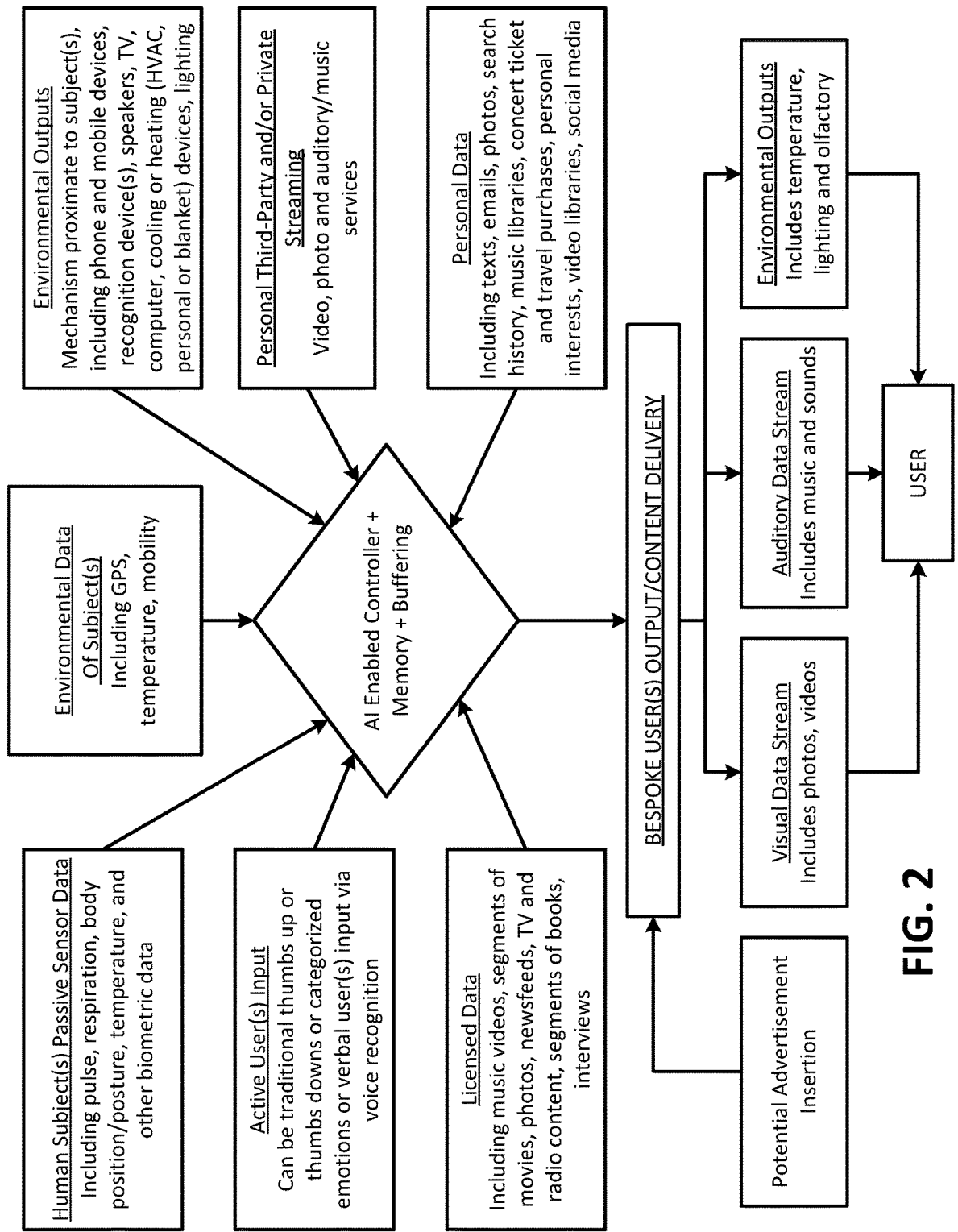
FIG. 2 is a flow chart illustrating other aspects of the invention.

FIG. 2 is a flowchart illustrating other aspects of the invention.

Many modifications and variations of the present invention are possible in light of the above teachings. It is, therefore, to be understood within the scope of the appended claims the invention may be protected otherwise than as specifically described.

I claim:

1. A system for transitioning or maintaining a user's state of consciousness comprising:
    a smart device having an interface configured to enable a first user to operate and provide feedback to the system, the smart device configured to receive inputs from a biometric device coupled to the first user of the system and an environmental sensor, and to control an audio/visual device and an environmental system based on the inputs from the biometric device, the feedback from the first user and the environmental sensor to facilitate the one of transitioning and maintaining a state of consciousness of the first user;
    a first biometric device coupled to the first user and configured to transmit the first user's biometric data to the smart device;
    a first environmental sensor configured to transmit environmental data to the smart device;
    a first environmental system coupled to the smart device, wherein the smart device is configured to control the first environmental system to optimize the first environmental system for transitioning the state of the first user; and,
    a first audio/visual device coupled to the smart device wherein the smart device is coupled to a database of personal images relevant to the first user and is configured to control audio and video output displayed on the first audio/visual device of the personal images to facilitate the one of transitioning and maintaining the state of consciousness of the first user;
    wherein the smart device includes artificial intelligence programming which analyses the biometric data and the environmental data transmitted to the smart device and provides a control signal to the first environmental system and to the first audio/visual device to optimize the first user's transitioning or maintaining the first user's state of consciousness; and
    wherein the smart device is configured to place the first user into a desired emotive state and to control the first environmental system and the first audio/visual device to create an autonomous sensory meridian response in the first user.

2. The system of claim 1, wherein the first biometric sensor is a heart rate monitor.

3. The system of claim 2, wherein the heart rate monitor is incorporated into a watch.

4. The system of claim 1, wherein the first environmental sensor is a temperature sensor.

5. The system of claim 1, wherein the first environmental sensor is a light sensor.

6. The system of claim 1, wherein the first environmental sensor is a sound sensor.

7. The system of claim 1, wherein the first environmental system is a heating, humidity, ventilation and air conditioning system.

8. The system of claim 1, wherein the first environmental system is a lighting system.

9. The system of claim 1, wherein the first environmental system is an olfactory device.

10. The system of claim 1, wherein the smart device is a computer.

11. The system of claim 1, wherein the smart device is a tablet device.

12. The system of claim 1, wherein the state of consciousness is one of a hypnagogic state and a hypnopompic state.

13. A method for facilitating a user's transitioning or maintaining a state of consciousness comprising:
    providing a controller;
    transmitting biometric data from a first user to the controller;
    transmitting environmental data of the environment proximate the first user to the controller;
    providing a database of personal images relevant to the first user coupled to the controller;
    transmitting feedback from the first user to the controller; and,
    controlling an environmental device to adjust the environment and an audio/visual device proximate the first user to display the personal images by the controller based on the biometric data, the feedback and the environmental data transmitted to the controller;
    wherein a desired emotive state of the first user is elicited by controlling at least one of the audio/visual device and the environmental device;
    wherein the controller includes artificial intelligence programming which analyses the biometric data and the environmental data transmitted to the controller and provides a control signal to the environmental device and to the audio/visual device to optimize the first user's transitioning or maintaining the first user's state of consciousness; and
    wherein the controller is configured to control the environmental device and the audio/visual device to create an autonomous sensory meridian response in the first user.

14. The method of claim 13, wherein the step of transmitting biometric data from a first user to the controller comprises:
    providing the first user with a heartrate monitoring device;
    periodically measuring the first user's heartrate with the device; and,
    electronically transmitting the first user's measured heartrate to the controller.

15. The method of claim 13, wherein the step of transmitting environmental data proximate the first user to the controller comprises:
    providing a temperature sensor proximate the first user;
    periodically measuring the temperature with the temperature sensor; and,
    electronically transmitting the measured temperature to the controller.

16. The method of claim 13, wherein the step of controlling an environmental device and an audio/visual device proximate the first user by the controller based on the biometric data and environmental data transmitted to the controller comprises:
    providing a heating device proximate the first user coupled to the controller;
    transmitting a signal from the controller to the heating device and subsequently adjusting a temperature output of the heating device by the controller.

17. The method of claim 13, wherein the controller is a computer.

* * * * *